United States Patent
Schroeter et al.

(10) Patent No.: US 10,274,608 B2
(45) Date of Patent: Apr. 30, 2019

(54) DETERMINING FUNCTIONAL DATA OF AN X-RAY DETECTOR

(71) Applicant: Siemens Aktiengesellschaft, München (DE)

(72) Inventors: Christian Schroeter, Bamberg (DE); Peter Sievers, Uttenreuth (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 549 days.

(21) Appl. No.: 15/002,436

(22) Filed: Jan. 21, 2016

(65) Prior Publication Data
US 2016/0220222 A1 Aug. 4, 2016

(30) Foreign Application Priority Data
Jan. 29, 2015 (DE) .................. 10 2015 201 494

(51) Int. Cl.
*A61B 6/00* (2006.01)
*G01T 1/00* (2006.01)
*G01T 1/24* (2006.01)
*G01T 7/00* (2006.01)

(52) U.S. Cl.
CPC .............. *G01T 1/00* (2013.01); *A61B 6/585* (2013.01); *G01T 1/24* (2013.01); *G01T 1/247* (2013.01); *G01T 7/005* (2013.01)

(58) Field of Classification Search
CPC .. G01T 1/00; G01T 1/24; G01T 1/247; G01T 7/005; A61B 6/585
See application file for complete search history.

(56) References Cited

U.S. PATENT DOCUMENTS

| | | | | |
|---|---|---|---|---|
| 5,200,625 | A * | 4/1993 | Kawai .................. | G01T 1/36 250/374 |
| 6,693,668 | B1 * | 2/2004 | May .................... | H04N 5/335 348/247 |
| 2004/0028181 | A1 * | 2/2004 | Charles, Jr. .......... | A61B 6/032 378/92 |
| 2007/0001865 | A1 * | 1/2007 | Rowe .................. | G08B 17/10 340/628 |
| 2011/0253886 | A1 * | 10/2011 | Hackenschmied ..... | G01T 1/249 250/252.1 |
| 2013/0108019 | A1 | 5/2013 | Tkaczyk et al. | |
| 2015/0362604 | A1 * | 12/2015 | Verbakel ............. | G01T 1/24 250/393 |

FOREIGN PATENT DOCUMENTS

| | | |
|---|---|---|
| DE | 102012205290 A1 | 10/2013 |
| WO | WO-2014132232 A2 | 9/2014 |

* cited by examiner

*Primary Examiner* — Chi-Cheng Kao
(74) *Attorney, Agent, or Firm* — Harness, Dickey & Pierce, P.L.C.

(57) ABSTRACT

A method is described for determining the polarization state of a sensor of an X-ray detector. In the method, the X-ray detector is illuminated with a sequence of light pulses wherein the individual pulses of the light pulse sequence have a different intensity. It is further determined at what intensity of the light pulses, charge pulses generated by the sensor of the X-ray detector exceed a threshold voltage of a signal detection circuit. Also described is a method for obtaining and/or setting functional data of a sensor of an X-ray detector and/or of a sensor illumination unit. Furthermore, an X-ray detector is described.

22 Claims, 5 Drawing Sheets

DETERMINING FUNCTIONAL DATA OF AN X-RAY DETECTOR

PRIORITY STATEMENT

The present application hereby claims priority under 35 U.S.C. § 119 to German patent application number DE 102015201494.0 filed Jan. 29, 2015, the entire contents of which are hereby incorporated herein by reference.

FIELD

At least one embodiment of the invention generally relates to a method for determining the polarization state of a sensor of an X-ray detector; a method for obtaining and/or setting functional data of a sensor and/or a sensor illumination unit; and/or an X-ray detector.

BACKGROUND

In medical examinations, for example, in computed tomography scans with the aid of X-rays, X-ray detectors are used. These X-ray detectors can be configured as scintillator detectors or as detectors with direct converters. In the following, X-ray detectors are taken to be any type of detector which either detects X-rays or other hard rays, such as gamma radiation.

In a detector made of a scintillator material, the scintillator material is excited on passage of the X-ray radiation and the excitation energy is output in the form of light. This visible light generated in the material is measured with the aid of photodiodes. The scintillator detector is typically configured in the manner of an array comprising a plurality of scintillator elements, wherein individual photodiodes are associated with the scintillator elements, so that the photodiodes also form an array.

Detectors with direct converters have semiconductor materials which carry out a direct conversion of the radiation incident thereupon into an electric signal. The incident X-ray radiation directly creates charge carriers in the form of electron-hole pairs. By applying a voltage (bias voltage) to the semiconductor material, the charge carrier pairs are separated by the electric field generated thereby and reach the electric contacts or electrodes which are mounted on the semiconductor material (see FIG. 1). By this means, an electric charge pulse is generated which is proportional to the absorbed energy and is evaluated by a downstream readout electronics system. Semiconductor detectors based, for example, on CdTe or CdZnTe and used in the field of human medical imaging have the advantage as compared with the scintillator detectors conventionally used there that with them an energy-sorting counting is possible, that is, depending on their energy, the X-ray quanta detected can be subdivided, for example, into two classes (high-energy and low-energy) or more.

On operation of semiconductor direct conversion radiation detectors such as, for example, detectors based on CdTe or CZT, under irradiation with gamma and X-ray radiation, particularly at high intensities, the phenomenon of polarization occurs. This is expressed in an unwanted change to the internal electric field in the semiconductor material of the detector. Due to the polarization, the charge carrier transportation properties and thus also the detector properties change. As a consequence, the pulse forms of the electrical signals corresponding to the X-ray quanta incident in the semiconductor layer, in particular the pulse height and the pulse width, are dependent to a significant degree on the polarization state of the semiconductor layer. The polarization effects are responsible for a reduction in the charge carrier mobility-lifetime product ($\mu\tau$ product) and therefore for an increase in the mean dwell time with simultaneous reduction of the lifetime of the charge carriers in the semiconductor material. The aforementioned polarization effects are essentially caused by defect sites in the form of vacancies or interstitial atoms during the manufacturing of the semiconductor layer. However, the polarization state of the semiconductor layer does not depend only on production-dependent parameters. It also depends on the temperature of the semiconductor material as well as on the history of the X-ray radiation impinging upon the semiconductor layer. The polarization state is thus changeable over time and is typically different between successive examinations, even before and after each individual examination.

In particular, the stated changes lead to a change in the signal properties of the measurement signal as a function of time. Expressed differently, due to the polarization, the intensity of the scan signal changes over time with a constant radiation dose. This phenomenon is known as "signal drift". A detector is constructed from a plurality of pixels. Since the signal drift of the individual pixels is different, for the detector there is a distribution of the signal drift factors associated with the individual pixels. Over time or under irradiation, this distribution changes and the width of the distribution of the signal drift factors increases significantly more strongly than the mean value of this distribution.

A possibility for reducing the signal drift lies in using the fact that the width of the distribution of the signal drift factors grows more strongly than the mean value of the distribution. A plurality of detectors are combined into groups of individual pixels known as "macropixels". These macropixels can comprise, for example, a number of 2×2, 3×3 or 4×4 individual pixels. In order to reduce the signal drift, individual pixels which drift strongly are entirely excluded from the signal transference. In this way, an improved drift behavior of the detector signal is achieved. However, this improvement is gained at the cost of a very great worsening in the detector efficiency, i.e. a signal usage that is worsened by, for example 6.25% to 25% and therefore also a correspondingly worsened signal-to-noise ratio (SNR) and/or a worsened dose utilization.

Another possibility for reducing the signal drift lies in the irradiation of the detector material with visible light or with infrared light in addition to or during the irradiation of the detector with X-ray radiation.

Furthermore, the possibility exists that a calibration of an X-ray detector is carried out during irradiation of the semiconductor layer of the X-ray detector. This makes use of the fact that a calibration is made more exactly if it is carried out taking account of the current polarization state of the semiconductor layer of the X-ray detector. This is the case, in particular, if the electrical signals are generated during the calibration process by means of a charge carrier transport in the semiconductor layer. This charge carrier transport is achieved by coupling light into the semiconductor layer wherein charge carrier clouds are generated which resemble those charge carrier clouds which typically arise through interaction of an X-ray quantum of a particular energy with the semiconductor layer.

Another conventional procedure lies in correcting the detector drift with a "pre-scan". Immediately before the image recording, a counting rate calibration takes place wherein the X-ray detector is irradiated with a dose rate bandwidth by variation of the tube current of an X-ray tube that is used, said dose rate bandwidth corresponding to the dose rate bandwidth to be expected at the X-ray detector during the later image recording.

A further source of measuring errors of X-ray detectors is caused by inhomogeneities in the sensor and the ASIC performing the readout.

In addition, it is also desirable to be able to test an X-ray scanner in advance for its correct functioning.

SUMMARY

An embodiment of the invention reduces inaccuracies arising due to the aforementioned causes during a scan made with the aid of X-ray detectors.

An embodiment of the invention is directed to a method for determining the polarization state of a sensor of an X-ray detector; an embodiment of the invention is directed to a method for obtaining and/or setting functional data of a sensor of an X-ray detector and/or a sensor illumination unit; and an embodiment of the invention is directed to an X-ray detector.

In the method according to an embodiment of the invention for determining the polarization state of a sensor of an X-ray detector, the sensor of the X-ray detector is illuminated with a sequence of light pulses wherein the individual pulses of the light pulse sequence have a different intensity. It is further determined at what intensity of the light pulses, charge pulses generated by the sensor of the X-ray detector exceed a pre-set threshold voltage of a signal detection circuit. Put another way, a relationship is created between a determined illumination intensity and the exceeded threshold voltage. Depending on the respective polarization state of the X-ray detector, different correlations are produced between the determined illumination intensity and the exceeded threshold voltage. Advantageously, the polarization state of the sensor can be determined in this way without the sensor having to be irradiated with X-rays.

In the method according to an embodiment of the invention for obtaining and/or setting functional data of a sensor and/or of a sensor illumination unit, the method according to an embodiment of the invention is used to determine the polarization state of a sensor of an X-ray detector. Thus, functional data of a sensor can be determined or functional values or parameters of the sensor can be set without any irradiation of the sensor with X-ray radiation having to be carried out.

The X-ray detector according to an embodiment of the invention comprises a sensor unit which is configured to generate a sensor signal according to a detected X-ray pulse. In addition, the X-ray detector according to an embodiment of the invention has a sensor illumination unit which is configured to illuminate the sensor unit with a light pulse sequence wherein individual pulses of the light pulse sequence have a different intensity. The X-ray detector according to an embodiment of the invention further comprises a signal detection unit which is configured to determine at what intensity of the light pulses, charge pulses generated by the sensor unit of the X-ray detector exceed a pre-set threshold voltage of a signal detection unit.

Further, particularly advantageous embodiments and developments of the invention are disclosed by the dependent claims and the following description. The X-ray detector according to an embodiment of the invention can also be further developed similarly to the dependent method claims. In addition, within the context of the invention, the various features of different example embodiments and claims can also be combined to new example embodiments.

In the method according to an embodiment of the invention for determining the polarization state of a sensor of an X-ray detector, the sensor of the X-ray detector is illuminated with a sequence of light pulses wherein the individual pulses of the light pulse sequence have a different intensity. It is further determined at what intensity of the light pulses, charge pulses generated by the sensor of the X-ray detector exceed a pre-set threshold voltage of a signal detection circuit. Put another way, a relationship is created between an illumination intensity and the determined exceeded threshold voltage. Depending on the respective polarization state of the X-ray detector, different correlations are produced between the illumination intensity and the determined exceeded threshold voltage. Advantageously, the polarization state of the sensor can be determined in this way without the sensor having to be irradiated with X-rays.

In the method according to an embodiment of the invention for obtaining and/or setting functional data of a sensor and/or of a sensor illumination unit, the method according to an embodiment of the invention is used to determine the polarization state of a sensor of an X-ray detector. Thus, functional data of a sensor can be determined or functional values or parameters of the sensor can be set without any irradiation of the sensor with X-ray radiation having to be carried out.

The X-ray detector according to an embodiment of the invention comprises a sensor unit which is configured to generate a sensor signal according to a detected X-ray pulse. In addition, the X-ray detector according to an embodiment of the invention has a sensor illumination unit which is configured to illuminate the sensor unit with a light pulse sequence wherein individual pulses of the light pulse sequence have a different intensity. The X-ray detector according to an embodiment of the invention further comprises a signal detection unit which is configured to determine at what intensity of the light pulses, charge pulses generated by the sensor unit of the X-ray detector exceed a pre-set threshold voltage of a signal detection unit.

Further, particularly advantageous embodiments and developments of the invention are disclosed by the dependent claims and the following description. The X-ray detector according to an embodiment of the invention can also be further developed similarly to the dependent method claims. In addition, within the context of the invention, the various features of different example embodiments and claims can also be combined to new example embodiments.

In a preferred variant of the method according to an embodiment of the invention for determining the polarization state of a sensor of an X-ray detector, the light pulse sequence comprises IR light pulses.

Preferably, the light pulses of the light pulse sequence have an intensity which rises or falls over time. With the aid of such a monotonously behaving light pulse sequence, for example, a pulse sequence with square pulses having a continuously rising or falling intensity, the exceeding of a threshold value can be determined particularly easily. A light pulse sequence of this type is particularly well suited to the calibration of detectors, but also of illumination units themselves, with which the light pulses are irradiated.

In a particularly preferred variant of the method according to an embodiment of the invention for obtaining and/or setting functional data of a sensor of an X-ray detector and/or of a sensor illumination unit, a signal drift of a sensor is determined. In this variant, firstly, the polarization state of the sensor is determined before the execution of an X-ray scan in accordance with the method according to an embodiment of the invention for determining the polarization state of a sensor of an X-ray detector. Subsequently, an X-ray recording of an object to be examined or of a partial region of an object to be examined is carried out with the aid of the X-ray detector. Following the X-ray scan, the polarization state of the sensor is again determined in accordance with the method according to an embodiment of the invention for determining the polarization state of a sensor of an X-ray detector.

Finally, the difference between the intensities of the light pulses which are associated with the exceeding of a particular pre-set threshold voltage and which were measured on determination of the polarization state of the sensor before the execution of the X-ray recording and the intensities of the light pulses which are associated with the exceeding of a particular pre-set threshold voltage and which were measured on determination of the polarization state of the sensor following the execution of the X-ray recording is determined. From the determined difference in the measured values before the X-ray recording and following the X-ray recording, the degree of signal drift due to the polarization of the semiconductor layer of the X-ray detector is concluded. In this way, the signal drift which prevails during an X-ray scan can be determined without an additional use of X-ray radiation.

In an alternative embodiment of the method according to an embodiment of the invention for obtaining and/or setting functional data of a sensor of an X-ray detector and/or of a sensor illumination unit, a sensor illumination unit is calibrated. A calibration should be understood in the following to be a measuring process for reliably reproducible determination and documentation of the deviation of a device used for determining measurement values relative to another measuring device.

In the calibration, the method according to an embodiment of the invention for determining the polarization state of a sensor of an X-ray detector with an already calibrated X-ray detector is carried out for a plurality of pixels of the calibrated X-ray detector. A type of indirect calibration is therefore carried out, since the measurement values determined with the already calibrated X-ray detector are used in order to deduce a deviation of the illumination intensity of the illumination device from a reference value. Based on the intensity values determined for different pixels, an illumination/intensity profile is determined for the sensor illumination unit. In this way, both local and global deviations of the intensity of the illumination unit are determined and this can be used, for example, for the improvement of the precision of further calibration processes with the aid of the now calibrated illumination unit.

In another alternative embodiment of the method according to the invention for obtaining and/or setting functional data of a sensor of an X-ray detector and/or of a sensor illumination unit, an energy calibration of the sensor of the X-ray detector is carried out. Herein, firstly, the method according to an embodiment of the invention for determining the polarization state of the sensor of an X-ray detector is applied to a plurality of pixels of the sensor of an X-ray detector. The illumination intensity values determined are subsequently correlated with the voltage threshold values used in the aforementioned method according to an embodiment of the invention for each of the plurality of pixels of the sensor of the X-ray detector. Finally, the X-ray energy values corresponding to the correlated illumination intensity values are determined as calibration data. The relationship between the illumination intensity values and the X-ray energy values can be determined, for example, on the basis of data from a preceding calibration of the illumination unit, as described above.

In a special embodiment of the method according to the invention in the variant in which an energy calibration of the sensor of an X-ray detector is carried out, the illumination intensity values determined are corrected with the aid of the illumination intensity profile determined with the method according to an embodiment of the invention in the variant of the calibration of a sensor illumination unit and during the correlation step, the corrected illumination intensity values are correlated with the voltage threshold values for each of the plurality of pixels of the sensor of the X-ray detector determined during the calibration. Differently expressed, the energy calibration takes place with an already calibrated illumination device taking account of the intensity profile determined during the calibration of the illumination device.

Herein, for the step of determining the X-ray energy values corresponding to the correlated illumination intensity values, a uniform relation, valid for all the pixels of the sensor of the X-ray detector, between the illumination intensity and the X-ray energy can be determined or alternatively, for each pixel individually, a relationship can be determined between illumination intensity and X-ray energy. In the latter variant, for example, a look-up table can be created which, during the calibration, with the aid of the illumination unit, correlates intensity values determined with the X-ray energy values of an already calibrated detector.

In addition, with the aid of the method for obtaining and/or for setting functional data of a sensor of an X-ray detector and/or a sensor illumination unit, it can be tested whether the pixels of a sensor are functioning and/or the connection between individual pixels and the signal detection units associated with each pixel are functioning or whether individual signal detection units are functioning.

Furthermore, with the aid of the method according to the invention for obtaining and/or setting functional data of a sensor of an X-ray detector and/or of a sensor illumination unit, an operational readiness of a detector can also be tested and/or whether energy threshold values of the detector are correctly stored in the signal detection units of the detector. The illumination with the aid of the sensor illumination unit in place of irradiation with the aid of an X-ray source is herein used as a test device.

Furthermore, using the method according to an embodiment of the invention for obtaining and/or setting functional data of a sensor of an X-ray detector and/or of a sensor illumination unit, it can also be determined whether a correct HV level exists at the sensor of the X-ray detector. Herein also, an illumination of the sensor of the X-ray detector is carried out with the aid of the sensor illumination unit in accordance with the scheme according to an embodiment of the invention. A comparison of the intensities and threshold values determined with corresponding reference values provides information on the correct functioning of the sensor.

Further possibilities for use of the method according to an embodiment of the invention for obtaining and/or setting functional data of a sensor of an X-ray detector and/or of a sensor illumination unit are a test of whether illumination units, for example LEDs, of the sensor illumination unit are functioning or a test in which it is determined whether the diffuser of the sensor illumination unit has become clouded.

It is particularly advantageous, when using the described method according to an embodiment of the invention, to select the pulse length of the light pulses such that, during creation of the individual pulses of the light pulse sequence, the pulse length and the light intensity of the pulses of the sensor illumination unit are decoupled from one another with a different intensity. In this way, inaccuracies due to the time-dependence of the pulse height of the voltage applied to the sensor illumination unit when changing the voltage applied to the sensor illumination unit on passing through of a pulse sequence are prevented.

When light pulses are generated, for example, current pulses whose amplitude is proportional to the light intensity of the light pulses can be used or alternatively voltage pulses which are correlated with light intensities, taking account of the characteristic curve of the light-emitting diodes used.

BRIEF DESCRIPTION OF THE DRAWINGS

The invention will now be described in greater detail making reference to example embodiments as illustrated in the accompanying drawings. In the various drawings, the same components are identified with identical reference signs. The drawings are generally not to scale. In the drawings.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Further, although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Figure 1:
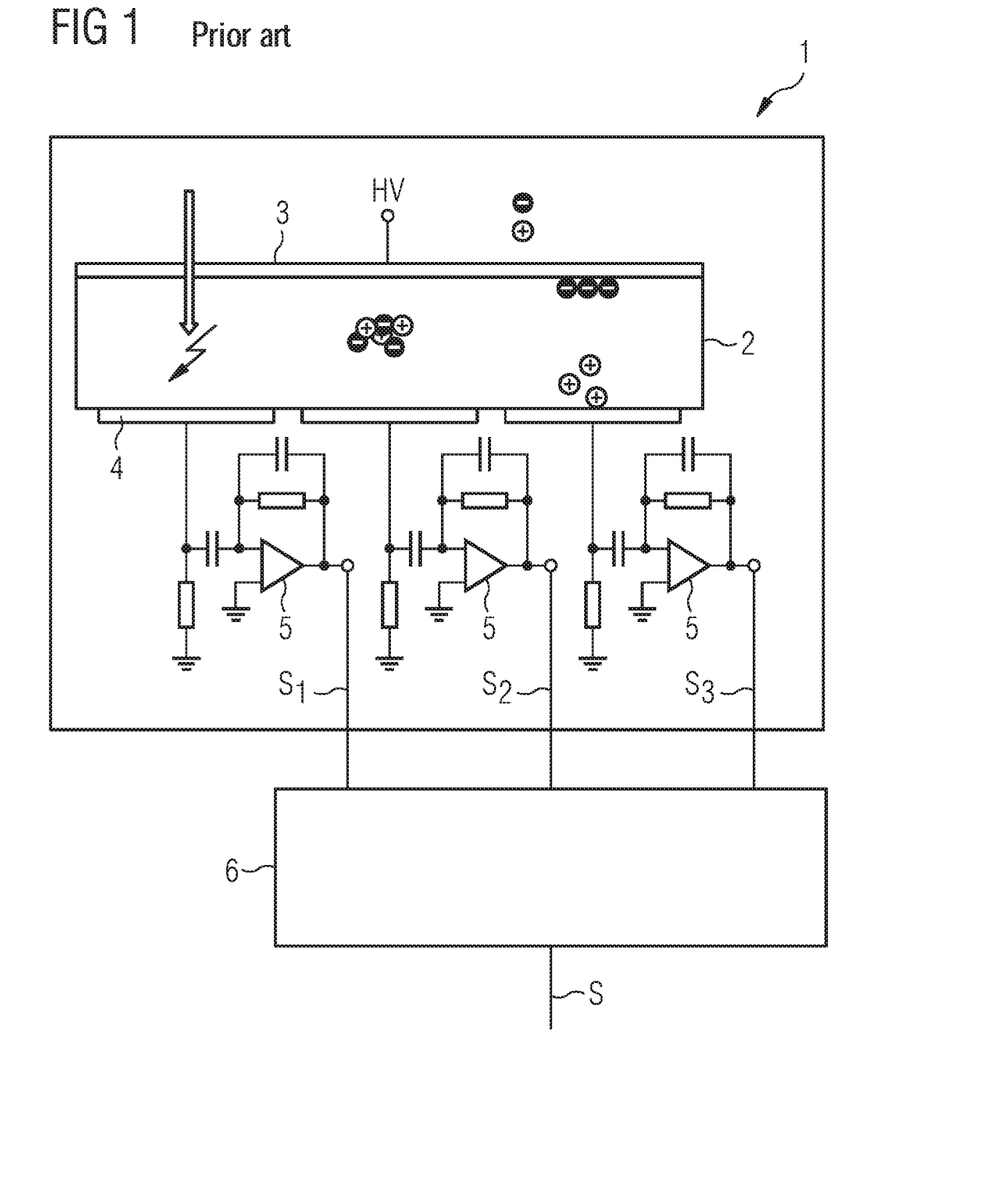
FIG. 1 is a schematic representation of the structure of a conventional X-ray detector which is configured as a direct converter.

In FIG. 1, the cross-section of a conventional semiconductor detector 1 which functions as a direct converter is shown. The semiconductor detector 1 is configured as a planar pixel detector. It comprises semiconductor material 2 in the form of a monocrystal as the detector material. The semiconductor material is covered on one side with a metal area which forms an electrical rear contact 3. A voltage is applied between the rear contact 3 and the pixel contacts 4.

The opposite side of the monocrystal 2 is covered with a structured metallization, the individual subsurfaces of which are configured as pixel contacts 4 and form, overall, a pixel matrix. The size and spacings of the pixel contacts 4 determine, together with further material parameters of the semiconductor material 2, the maximum spatial resolving power of the detector 1. The resolution typically lies in the range from 10 to 500 µm. The individual pixel contacts 4 are each connected to separate readout electronic circuits 5 with which measurement signals $s_1$, $s_2$, $s_3$ are detected.

Furthermore, the detector comprises an adding element 6, with which the measurement signals $s_1$, $s_2$, $s_3$ are added together into a macropixel signal S.

It should be noted that the arrangement 1 in FIG. 1 is shown as a cross-section and therefore the arrangement 1 in FIG. 1 comprises a total of 9 pixel contacts. For greater clarity, in accordance with the cross-section, only 3 pixel contacts have been drawn per macropixel. As previously mentioned, 4, 16 or another number of pixel contacts per macropixel are also usual.

The detector 1 shown in FIG. 1 functions as follows: X-ray radiation incident on the detector 1 causes interactions of the X-ray quanta with the semiconductor material 2 of the detector 1 wherein electron-hole pairs are generated. The voltage HV applied to the contacts of the detector generates an electric field which moves the charge carriers created toward the electrical contacts, particularly toward the pixel contacts 4. The charge concentration at the electrodes or pixel contacts 4 of the detector 1 generates an electric charge pulse which is proportional to the absorbed energy of the X-ray radiation. This charge pulse is read out by the attached readout electronics system 5 which is also known as the signal detection circuit or signal detection unit. The pixel signals $s_1$, $s_2$, $s_3$ detected by the readout electronics system 5 are passed on to an adding unit 6 which adds the measurement signals $s_1$, $s_2$, $s_3$ (actually the measurement signals $s_1$ to $s_9$) into a macropixel signal S. The signals do not necessarily have to be grouped together; as an alternative, the individual signals from individual pixel contacts can also be read out directly.

Figure 9:
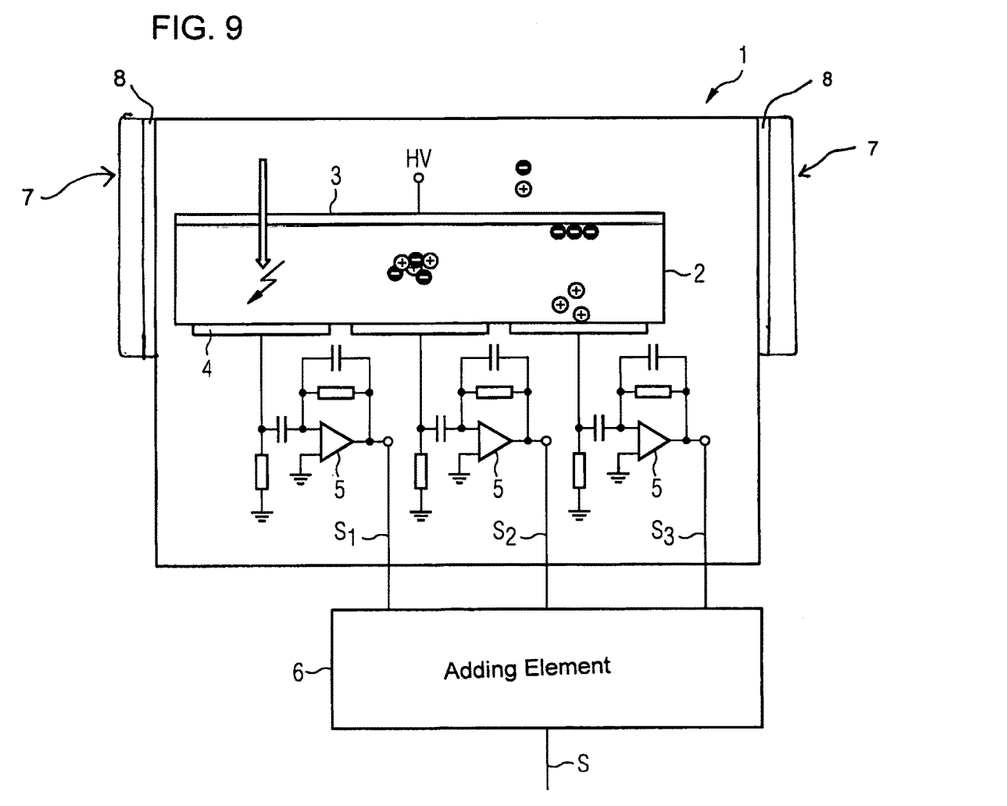
FIG. 9 is a schematic representation of an example structure of an X-ray detector according to an example embodiment of the invention.

The X-ray detector 1 according to an embodiment of the invention shown in FIG. 9 includes a sensor unit 2, 3, 4 which is configured to generate a sensor signal according to a detected X-ray pulse. In addition, the X-ray detector 1 according to an embodiment of the invention has a sensor illumination unit 7 which is configured to illuminate the sensor unit 2, 3, 4 with a light pulse sequence wherein individual pulses of the light pulse sequence have a different intensity. According to an embodiment of the invention for obtaining and/or setting functional data of a sensor of an X-ray detector 1 and/or of a sensor illumination unit 7 are a test of whether illumination units, for example LEDs, of the sensor illumination unit are functioning or a test in which it is determined whether a diffuser 8 of the sensor illumination unit 7 has become clouded.

Figures 2, 3:
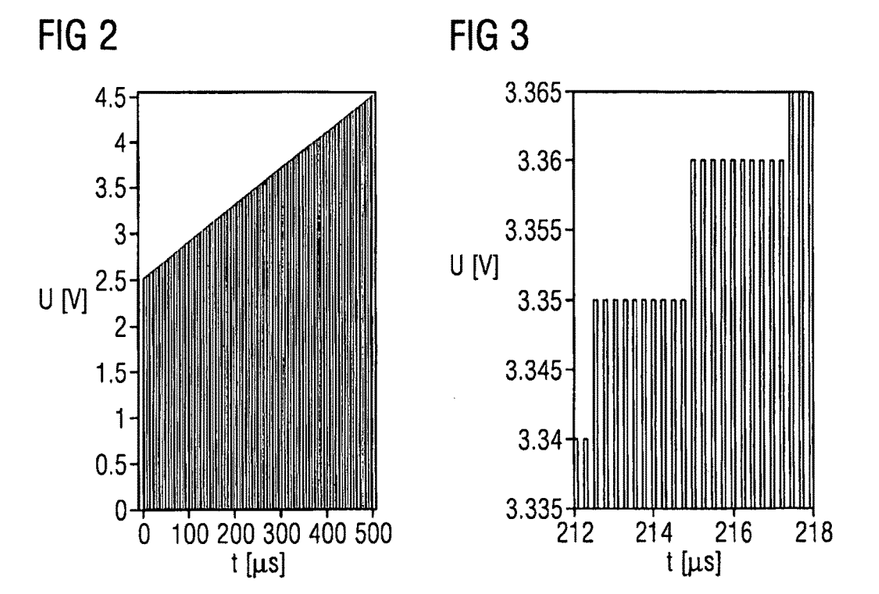
FIG. 2 is a graphical representation which illustrates schematically the variation over time of a monotonically rising IR pulse sequence.
FIG. 3 is an enlarged portion of the graphical representation of FIG. 2.

FIG. 2 shows a pulse sequence of an illumination unit, in this case an IR illumination unit for illuminating an X-ray detector. Herein, the electric voltage U applied to the IR illumination unit which correlates with the illumination intensity is plotted over time t. The triangular form of the pulse sequence is also designated a triangular spectrum. As FIG. 3 shows, the voltage pulses with which the IR illumination unit is operated are kept constant for a pre-determined constant time interval of, for example, 2 µs. In a calibrated detector, using an IR ramp of this type, the IR intensity or the LED voltage or a corresponding LED current can be determined, above which the charge pulses generated in the sensor of the detector exceed a pre-set threshold in the signal detection circuit, for example, an ASIC. Differently expressed, an IR intensity image is derived from the determination of the intensity values, providing information over the polarization state of the sensor.

Figure 4:
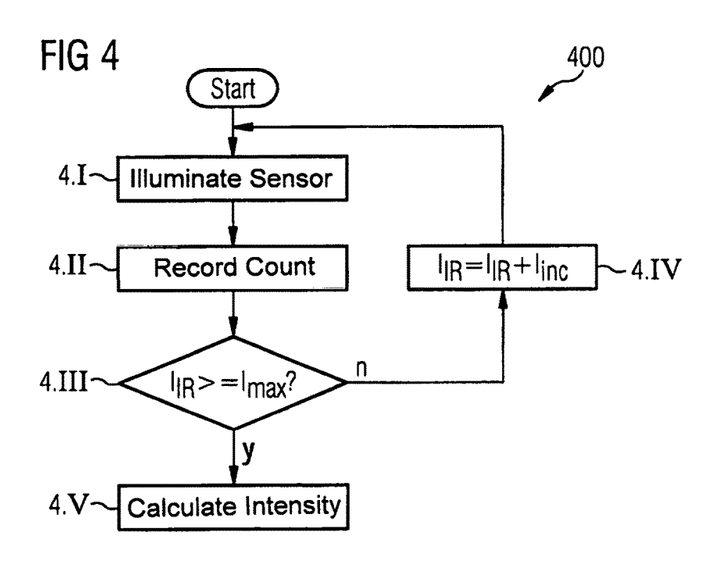
FIG. 4 is a flow diagram which shows schematically a method for determining the polarization state of a sensor of an X-ray detector according to an example embodiment.

FIG. 4 shows a flow diagram which illustrates a method 400 for determining the polarization state of a sensor of an X-ray detector according to an example embodiment of the invention.

At the start, an initial value for the current $I_{IR}$ flowing through the LED is selected. In step 4.I, a sensor of an X-ray detector is illuminated with IR light, for example with the aid of an IR-LED, wherein the current flowing through the IR-LED has a current strength $I_{IR}$. In step 4.II, if a sensor voltage which exceeds a sensor threshold value is generated by the IR light waves incident upon the sensor, a count result is recorded. In step 4.III, it is determined whether the pre-set intensity of the IR pulses or the current strength $I_{IR}$ proportional thereto of the IR-LED reaches or exceeds a maximum value $I_{max}$. If this is not the case, as indicated in FIG. 4 by "n", in step 4.IV, the electric current strength $I_{IR}$ of the current flowing through the IR illumination unit, i.e. the IR-LED, is increased by a particular increment current strength $I_{inc}$.

Subsequently, the sequence returns to step 4.I and the sensor of the X-ray detector is irradiated with IR light, wherein however an electric current $I_{IR}$ with an increased current strength now flows through the IR-LED. Subsequently, in step 4.II, if a sensor voltage which exceeds a sensor threshold value is generated by the IR light waves incident upon the sensor, a count result is recorded. In step 4.III, it is determined whether the pre-set intensity of the IR pulses or the current strength $I_{IR}$ proportional thereto of the IR-LED reaches or exceeds a maximum value $I_{max}$. If this is now the case, as indicated in FIG. 4 with "y", then in the step 4.V, based on the number of detected count results and given the knowledge regarding the variation and the shape of the pulse sequence (in this case, the variation is linear) the intensity at which the detector began to count, i.e. at which a voltage threshold value of the detector was exceeded is calculated. The determined intensity value of the LED or alternatively, the current strength $I_{IR}$ of the electric current flowing through the LED is thus correlated with the respective pre-set threshold value of the sensor. For example, the pre-set threshold voltage corresponds to a DAC (digital analogue converter) value of the signal detection unit of the sensor, which can now be correlated with the determined intensity of the IR illumination. The determined correlation gives information about the polarization state of the sensor of the X-ray detector. For example, it may be that, due to the polarization, with the same DAC value, a count result is only/already achieved at a higher/lower intensity value of the IR illumination than without polarization. This phenomenon corresponds to the aforementioned signal drift.

Figure 5:
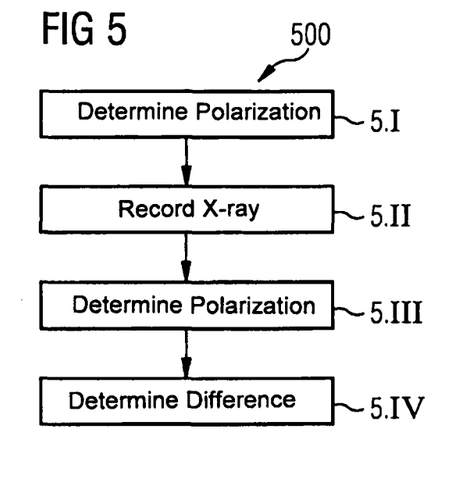
FIG. 5 is a flow diagram which illustrates schematically a method for determining the signal drift of a sensor of an X-ray detector according to an example embodiment of the invention.

FIG. 5 shows a method 500 for determining the signal drift of a sensor of an X-ray detector according to an example embodiment of the invention. In step 5.I, firstly, the polarization state of the sensor is determined before the execution of an X-ray scan in accordance with the method illustrated in FIG. 4 for determining the polarization state of a sensor of an X-ray detector. Subsequently, in step 5.II, an X-ray recording is created with the aid of the X-ray detector. For example, a CT image of a patient is generated. Subsequently in step 5.III, the polarization state of the sensor is determined after the execution of the X-ray recording in accordance with the method illustrated in FIG. 4 for determining the polarization state of a sensor of an X-ray detector. Finally, in step 5.IV, the difference of the two polarization states is determined, which is correlated with the signal drift. Otherwise expressed, in steps 5.I and 5.III, intensity values or the current values $I_{IR}$ associated therewith or voltage values UIR correlated therewith of IR pulses which are associated with the exceeding of a particular pre-set threshold voltage or a DAC value correlated therewith of a detection circuit are determined. If in step 5.III, other intensity values or LED current values $I_{IR}$ correlated therewith or voltage values UIR correlated therewith of the IR illumination unit are determined at the same DAC value, then the signal drift correlates with the difference of the determined IR intensities and can thus be corrected.

Figure 6:
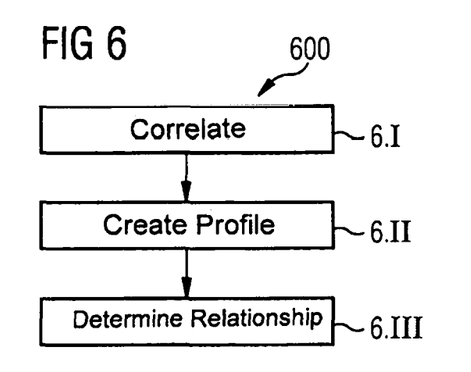
FIG. 6 is a flow diagram which illustrates a method for calibrating a lighting unit according to an example embodiment of the invention.

FIG. 6 illustrates a method 600 for calibrating an IR illuminating unit according to an example embodiment of the invention. In step 6.I, the method illustrated in FIG. 4 is carried out with an already calibrated X-ray detector for a plurality of pixels of the calibrated X-ray detector. Through correlation of the respectively measured IR intensity values or the current values $I_{IR}$ correlated therewith of the illumination device, wherein a particular pixel of the already calibrated X-ray detector achieves a voltage pulse with a voltage value which exceeds a pre-determined voltage threshold, with the previously known voltage threshold values of the already calibrated X-ray detector, in step 6.II, a type of map of an intensity profile is created which gives information concerning the homogeneity of the LED light guide and lens system. In step 6.III, in addition, a correlation of the measured IR intensity values with a corresponding X-ray energy of the already calibrated X-ray detector is undertaken, this arising from the correlation determined during the calibration of the already calibrated X-ray detector between the X-ray energy and the respective threshold value of the signal detection circuit for a respective pixel. Once the relationship determined in step 6.III is known, with the aid of the thus calibrated IR illumination device, any desired still uncalibrated X-ray irradiation unit can now be calibrated without being subjected to X-ray radiation.

Figure 7:
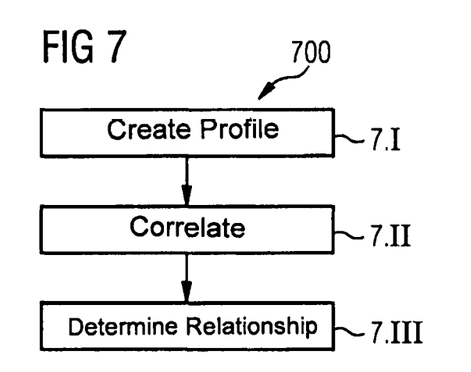
FIG. 7 is a flow diagram which illustrates a method for carrying out an energy calibration of a sensor of an X-ray detector according to an example embodiment of the invention.

FIG. 7 illustrates a method 700 for carrying out an energy calibration of a sensor of an X-ray detector.

In order to take account of inhomogeneities in the IR illumination, in step 7.I, an intensity profile of the IR illumination is created during illumination of an already calibrated sensor system, as illustrated by the flow diagram in FIG. 6.

In step 7.II, the method shown in FIG. 4 is applied to a plurality of pixels of the sensor to be calibrated of the X-ray detector. The IR intensity values thereby determined are correlated with the pre-determined voltage threshold values for each of the plurality of pixels of the sensor of the X-ray detector. In step 7.II, a type of threshold scan can be carried out wherein the threshold voltage is adjusted by changing the DAC values after executing step 7.II and step 7.II is repeated with the new DAC value. In order to take account of inhomogeneities in the IR illumination, the IR intensity values determines are corrected by the intensity profile determined in step 7.I. In step 7.III, the corresponding X-ray energy values are associated with the correlated IR intensity values. The relationship between the X-ray energy values and the IR intensity values has been determined, for example, during the calibration of the IR illumination device. Advantageously, the X-ray sensor can be calibrated without the use of X-ray radiation so that radiation exposure during the calibration is prevented.

Figure 8:
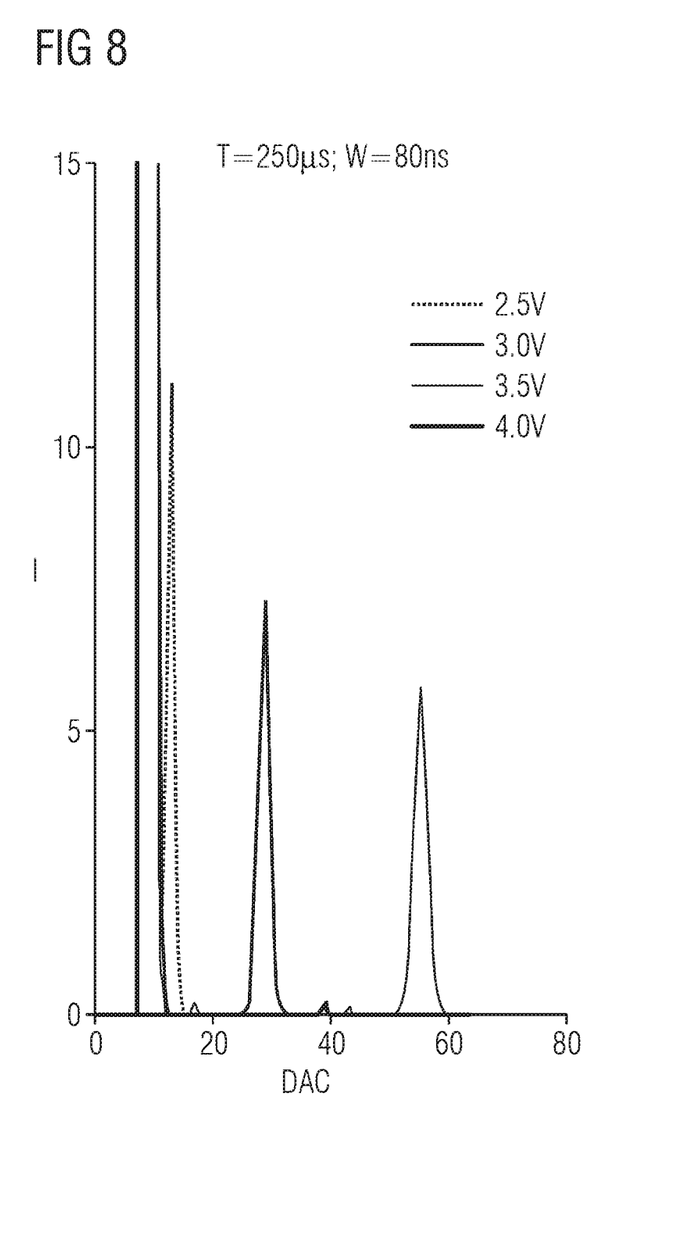
FIG. 8 is a graph which illustrates the energy calibration for a pixel of a sensor.

In FIG. 8, the result of the procedure shown in FIG. 7 for a single pixel of a sensor of a detector is illustrated. Herein, the derivative of the sensor signal intensity I is plotted against the DAC value of the detection circuit. The IR intensities or the LED voltages $U_{IR}$ correlated therewith determined for the individual DAC values which are associated with the peaks shown in the graph are given at top right in the legend of the graph. For example, a voltage $U_{IR}$=2.5V is correlated with a DAC value of approximately 15, a voltage $U_{IR}$=3.0V is correlated with a DAC value of approximately 30 and a voltage $U_{IR}$=3.5V is correlated with a DAC value of approximately 55. From the determined IR intensities, the X-ray energy values of the threshold values of the sensor associated with the DAC values can now be concluded. Herein, X-ray energy values are used which have been correlated during the calibration of the illumination device with the IR intensities of the illumination device. A procedure of this type can be carried out pixel for pixel so that pixel-accurate calibration is enabled. The periodicity T used in this actual example of use, that is the time which elapses until a new voltage pulse is emitted to the LEDs of the illumination unit is, in this case, 250 μs and the duration W of the respective voltage pulse in this special case is 80 ns. In this case, a scan was carried out with a constant voltage or intensity in each case.

In order to take account of aging or clouding of the LED light guide and lens system, the overall intensity of the IR illumination device can be readjusted or calibrated by means of a measurement of the HV current. Furthermore, by means of such a readjustment, tolerance variations in the manufacturing of the electrode can be intercepted since, during norming via the HV current, only IR photons that have been absorbed within the active volume can contribute to the current.

Finally, it should again be noted that the detailed methods and constructions described above are example embodiments and the basic principle can also be varied over a wide range by a person skilled in the art without departing from the field of the invention as defined by the claims. In particular, in place of IR illumination units, illumination units with spectra in the visible region or other frequency regions can also be used.

For the sake of completeness, it should be mentioned that the use of the indefinite article "a" or "an" does not preclude the relevant feature also from being present plurally. Similarly, the expression "unit" does not preclude this consisting of a plurality of components which may possibly also be spatially distributed.

The aforementioned description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods. Further, elements and/or features of different example embodiments may be combined with each other and/or substituted for each other within the scope of this disclosure and appended claims.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a polarization state of a sensor of an X-ray detector, comprising:
    illuminating the X-ray detector with a sequence of light pulses, individual ones of the light pulses of the light pulse sequence including different intensities;
    determining above which intensity of the light pulses, charge pulses generated by the sensor of the X-ray detector exceed a threshold voltage of a signal detection circuit; and
    determining the polarization state from a correlation of the determined illumination intensity and the exceeded threshold voltage.

2. The method of claim 1, wherein at least one of
    the light pulse sequence includes IR light pulses, and
    the light pulse sequence includes an intensity which rises or falls over time.

3. A method for at least one of obtaining and setting functional data of a sensor of at least one of an X-ray detector and an illumination unit, the method comprising:
    applying the method of claim 2.

4. The method of claim 1, wherein the determination of the polarization state of the sensor of the X-ray detector is achieved by the determining.

5. A method comprising:
    applying a method, for determining a polarization state of a sensor of an X-ray detector, to at least one of obtain and set functional data of at least one of a sensor of an X-ray detector and an illumination unit, the method for determining the polarization state of the sensor of the X-ray detector including
        illuminating the X-ray detector with a sequence of light pulses, individual ones of the light pulses of the light pulse sequence including different intensities;
        determining above which intensity of the light pulses, charge pulses generated by the sensor of the X-ray detector exceed a threshold voltage of a signal detection circuit; and
        determining the polarization state from a correlation of determined illumination intensity and an exceeded threshold voltage, wherein determination of the polarization state of the sensor of the X-ray detector is achieved by the determining.

6. The method of claim 5, further comprising:
    determining a polarization state of the sensor of the X-ray detector before performing an X-ray scan;
    carrying out an X-ray scan with the aid of the X-ray detector;
    determining the polarization state of the sensor of the X-ray detector after the performance of the X-ray scan; and
    determining a difference between the intensities of the light pulses associated with exceeding of a particular pre-set threshold voltage and measured on determination of the polarization state of the sensor before and after the performance of the X-ray scan.

7. The method as claimed in claim 6, further comprising:
    carrying out, based on a determined change in the polarization state, a correction of an X-ray image scan.

8. The method of claim 5, further comprising:
    carrying out the method, for determining the polarization state of the sensor of the X-ray detector, with an already calibrated X-ray detector for a plurality of pixels of the calibrated X-ray detector; and
    determining an illumination intensity profile of the illumination unit, based on intensity values determined for different pixels as calibration data.

9. The method of claim 8, further comprising:
    applying the method for determining the polarization state of the sensor of the X-ray detector, on a plurality of pixels of the sensor of the X-ray detector;
    correlating determined illumination intensity values with voltage threshold values, used in the method for determining the polarization state of the sensor of the X-ray detector, for each of the plurality of pixels of the sensor of the X-ray detector; and
    determining, from the correlated illumination intensity values, corresponding X-ray energy values as calibration data.

10. The method of claim 9, wherein the determined illumination intensity values are corrected with the aid of the illumination intensity profile determined and in the correlation, the corrected illumination intensity values are correlated with the voltage threshold values used in the method for determining the polarization state of the sensor of the X-ray detector, for each of the plurality of pixels of the sensor of the X-ray detector.

11. The method of claim 10, wherein for the determining of the X-ray energy values corresponding to the correlated illumination intensity values, a uniform relation valid for all the pixels of the sensor of the X-ray detector between the illumination intensity and the X-ray energy is determined or for each pixel individually, a relationship between illumination intensity and X-ray energy is determined.

12. The method of claim 9, wherein for the determining of the X-ray energy values corresponding to the correlated illumination intensity values, a uniform relation valid for all the pixels of the sensor of the X-ray detector between the illumination intensity and X-ray energy is determined or for each pixel individually, a relationship between illumination intensity and X-ray energy is determined.

13. The method of claim 5, further comprising testing at least one of
    whether pixels of a sensor are functioning,
    whether connection between individual pixels and a signal detection unit associated with each pixel is functioning, and
    whether individual signal detection units are functioning.

14. The method of claim 5, further comprising testing at least one of
    an operational readiness of a detector, and
    whether energy threshold values of the detector are correctly stored in signal detection units of the detector.

15. The method of claim 5, further comprising determining whether a corrected HV level has been applied to the sensor of the X-ray detector.

16. The method of claim 5, further comprising at least one of
    determining whether illumination units of the illumination unit are functioning and determining whether a diffuser of the illumination unit has become cloudy.

17. The method of claim 5, wherein a pulse length of the light pulses is selected such that, during creation of the individual pulses of the light pulse sequence, the pulse length and the light intensity of the pulses of the illumination unit are decoupled from one another with a different intensity.

18. The method of claim 5, wherein at least one of
the light pulse sequence includes IR light pulses, and
the light pulse sequence includes an intensity which rises or falls over time.

19. The method of claim 18, further comprising:
carrying out the method, for determining the polarization state of the sensor of the X-ray detector, with an already calibrated X-ray detector for a plurality of pixels of the calibrated X-ray detector; and
determining an illumination/intensity profile of the illumination unit, based on intensity values determined for different pixels as calibration data.

20. The method of claim 18, further comprising:
applying the method, for determining the polarization state of the sensor of the X-ray detector, on a plurality of pixels of the sensor of the X-ray detector;
correlating determined illumination intensity values with voltage threshold values, used in the method for determining the polarization state of the sensor of the X-ray detector, for each of the plurality of pixels of the sensor of the X-ray detector; and
determining, from the correlated illumination intensity values, corresponding X-ray energy values as calibration data.

21. The method of claim 5, further comprising:
applying the method, for determining the polarization state of the sensor of the X-ray detector, on a plurality of pixels of the sensor of the X-ray detector;
correlating determined illumination intensity values with voltage threshold values, used in the method for determining the polarization state of the sensor of the X-ray detector, for each of the plurality of pixels of the sensor of the X-ray detector; and
determining, from the correlated illumination intensity values, corresponding X-ray energy values as calibration data.

22. An X-ray detector, comprising:
a sensor unit, configured to generate a sensor signal according to a detected X-ray pulse;
a sensor illumination unit, configured to illuminate the sensor unit with a light pulse sequence wherein individual pulses of the light pulse sequence have a different intensity; and
a signal detection unit, configured to determine at what intensity of the light pulses, charge pulses generated by the sensor unit of the X-ray detector exceed a threshold voltage of a signal detection unit and configured to determine a polarization state from a correlation of a determined illumination intensity and an exceeded threshold voltage.

* * * * *